US005798362A

United States Patent [19]
Leonardi et al.

[11] Patent Number: 5,798,362
[45] Date of Patent: Aug. 25, 1998

[54] QUINAZOLINYL-AMINO DERIVATIVES HAVING α-ANTAGONIST ACTIVITY

[75] Inventors: Amedeo Leonardi, Milan; Gianni Motta, Barlassina; Carlo Boi, Cinisello Balsamo; Rodolfo Testa, Vignate, all of Italy

[73] Assignee: Recordati S.A. Chemical and Pharmaceutical Company, Chiasso, Switzerland

[21] Appl. No.: 716,160

[22] PCT Filed: Mar. 17, 1995

[86] PCT No.: PCT/EP95/01001

§ 371 Date: Sep. 17, 1996

§ 102(e) Date: Sep. 17, 1996

[87] PCT Pub. No.: WO95/25726

PCT Pub. Date: Sep. 28, 1995

[30] Foreign Application Priority Data

Mar. 18, 1994 [IT] Italy .................. MI94A0506

[51] Int. Cl.$^6$ .................. A61K 31/505; C07D 403/04
[52] U.S. Cl. .................. 514/260; 544/284; 544/291; 514/259
[58] Field of Search .................. 514/259, 260; 544/293, 291, 284

[56] References Cited

U.S. PATENT DOCUMENTS

| | | | |
|---|---|---|---|
| 3,511,836 | 5/1970 | Hess | 544/284 |
| 3,635,979 | 1/1972 | Hess | 544/284 |
| 4,026,894 | 5/1977 | Winn et al. | 260/256.4 |
| 4,044,136 | 8/1977 | Danilewicz et al. | 424/251 |
| 4,062,844 | 12/1977 | Hammen | 544/284 |
| 5,110,927 | 5/1992 | Pitha et al. | 514/259 |

FOREIGN PATENT DOCUMENTS

| | | |
|---|---|---|
| 0 028 031 A1 | 5/1981 | European Pat. Off. . |
| 0 225 866 A2 | 6/1987 | European Pat. Off. . |
| 2 389 614 | 12/1978 | France . |
| 925468 | 3/1955 | Germany . |
| 2 143 730 | 3/1973 | Germany . |
| 34 19 223 A1 | 6/1984 | Germany . |
| 679676 | 9/1952 | United Kingdom . |
| 2 068 961 | 8/1991 | United Kingdom . |

OTHER PUBLICATIONS

Form PCT/ISA/210 for PCT/EP95/01001.
Theodora W. Greene and Peter G. M. Wuts, "Protective Groups In Organic Synthesis," A Whiley-Interscience Publication, pp. 335-337 (1991).
Marc Julia, "Sur Quelques Nouveauz Dérivés Aryloxyisobutyriques Et Apparentés," Bull. Soc. Chim. France, pp. 776-783 (1956).
Giulio Audisio e Ruggero Ruggieri, "Ricerche su Derivati Dell'acido α-psso-isobutirrico," Gazz. Chim. It., 93 pp. 335-338 (1963).
William S. Johnson et al., "An Approach to Taxodione Involving Biomimetic Polyene Cyclization methodology," Tetrahedron, vol. 38, vol. 10, pp. 1397-1404 (1982).

T.H. Althuis and H.J. Hess, "Synthesis and Identification of the Major Metabolites of Prazosin Formed in Dog and Rat," Journal of Medicinal Chemistry, vol. 20, No. 1, pp. 146-149 (1977).

K.E. Hamlin et al., "Histamine Antagonists. II.[1] Unsymmetrical I, 4–Disubstituted Piperazines," J. Am. Chem. Soc. 71, pp. 2731-2734 (1949).

J. Pitha et al., "Reduction of Carboxylic Acids and Their Derivatives With Sodium Aluminum Hydride," Collection Czech. Chem. Communs. 25, pp. 736-742 (1960) [CA 54, 13055h (1960)].

I. Csiba et al., "67041g Solubilization properties of some water-soluble aryl alkyl ether derivaties. I Preparation and solubilization properties of aryloxyacetic acids," Cesk. Farm. 17, pp. 28-33 (1968) [CA 69, 67041g (1968)].

S.V. Kessar et al., "Azasteroids: Part XII–Synthesis of (+)-I3, I6–Diaza-I5–oxo–I8–norequilenin Methyl Ether," Indian J. of Chem. 12, pp. 113-116 (1974).

Von H. Schaefer et al., "Synthese, physikalisch–chemische Eigenschaften und orientierende pharmakologische Untersuchungen von Budipin und verwandten 4,4–Diphenylpiperidinen[1])," Arzneim.-Forsch. 34, pp. 233-240 (1984).

John B. Stenlake et al., "Neuromuscular blocking agents Sterochemical studies on 1–benzyltetrahydroisoquinolinium salts," Eur. J. Med. Chem.-Chim. Ther. 9, pp. 233-238 (1974).

Carrol S. Weil, "Tables for Convenient Calculation of Median–effective Dose ($LD_{20}$ OR $ED_{20}$) And Instructions In Their Use," Biometrics, 8, p. 249 (1952).

Debra Schwinn et al., "Molecular Cloning and Expression of the cDNA for a Novel $\alpha_1$–Adrenergic Receptor Sybtype," J. Biol. Chem., 265, pp. 8184-8189 (1990).

Susanna Cotecchia et al., "Molecular cloning and expression of the cDNA for the hamster $\alpha_1$–adrenergic receptor," Proc. Natl. Acad. Sci. USA, vol. 85, pp. 7159-7163 (Oct. 1988).

Jon W. Lomasney et al., "Molecular Cloning and Expression of the cDNA for a Novel $\alpha_{1A}$–Adrenergic Receptor Sybtype," J. Biol. Chem. 266, pp. 6365-6369 (1991).

De Lean et al., "Simultaneous analysis of families of sigmoidal curves: application to bioassay, radioligand assay, and physiological dose–response curves," Am. J. Physiol. 235, pp. E97-102 (1978).

Primary Examiner—Matthew V. Grumbling
Attorney, Agent, or Firm—Finnegan, Henderson, Farabow, Garrett & Dunner, L.L.P.

[57] ABSTRACT

New qunazolinyl-amino derivatives useful as $\alpha_1$-adrenoreceptor blockers are described. These compounds can be used as therapeutic agents for treating afflictions and diseases related to hyperactivity of the α-adrenergic system, such as, for example, arterial hypertension, prostate benign hyperplasia, high intraocular pressure and hpercholesterolemia. Processes for the preparation of the above said compounds are also described.

30 Claims, No Drawings

QUINAZOLINYL-AMINO DERIVATIVES HAVING α-ANTAGONIST ACTIVITY

This is a 35 USC §371 national stage application based on PCT/EP94/01001, filed Mar. 17, 1995.

The present invention refers to new derivatives of 4-amino-6,7-dimethoxyquinazoline having α-antagonist activity, their isomeric mixtures, the enantiomers, their addition salts with pharmaceutically acceptable acids or the pharmaceutical compositions containing them. Among the quinazoline derivatives already known, in particular those comprising in their structure the piperazine-group, many present an antihypertensive or hypotensive activity both systemic and intraocular, and also a regulating activity on the biosynthesis of cholesterole. For example U.S. Pat. No. 3,511,836 describes quinazoline-derivatives having antihypertensive action. In particular among the described compounds the 1-(4-amino-6,7-dimethoxy-2-quinazolinyl)-4-(2-furanylcarbonyl)piperazine (Prasozine) is actually used for this kind of therapy.

In U.S. Pat. No. 4,026,894 other compounds structurally related to the above said are described, among them the 1(4-amino-6,7-dimethoxy-2-quinazolinyl)-4-[(tetrahydro-2-furanyl)-carbonyl)]piperazine (Terazosine) is used as hypotensive agent and in the therapy of prostate benign hyperplasia (BPH).

However, in the therapeutical treatment with the above said compounds, some undesired side effects where observed, such as: cephalea, somnolence, asthenia, nausea, palpitation. In some cases also postural effects were observed in conjunction with the usual symptoms associated with the decreasing of pressure, i.e. vertigo and lightheaded. It is therefore still desired to develop substances which, although therapeutically active against the above said disorders, show less marked side effects.

U.S. Pat. No. 5,110,927 describes prazosin analogues substituted at position 4 of the piperazinyl ring with a wide-variety of substituents, such as phenylaminothiocarbonyl, cinnamoyl or bicyclooctadienecarbonyl residues, as well as with the 2-phenylethylcarbonyl, the phenoxymethylcarbonyl, the 2-naphtylcarbonyl or the phenylaminocarbonyl group.

GB-A-2,068,961 and EP-A-28031 disclose antihypertensive 4-amino-6,7-dimethoxy-quinazolines substituted at position 2 with a substituted piperazinyl or homopiperazinyl ring, and disclose in particular the 2-piperazinyl-quinazolines substituted at position 4 of the piperazinyl ring with a phenylalkylcarbonyl or a phenooxyalkylcarbonyl residue (GB-A-2.068.961), or with an optionally substituted phenylaminocarbonyl residue (EP-A-28031).

U.S. Pat. No. 4,062,844 reports antihypertensive 4-amino-2-(1-piperazinyl)-6,7-dimethoxy-quinazolines substituted at position 4 of the piperazinyl ring with a wide range of groups, such as a phenylcarbonyl, an alkyloxycarbonyl, an (unsubstituted-phenoxy)carbonyl group or a dialkylaminocarbonyl group.

Other known antihypertensive compounds are the 4-amino-6,7-dimethoxy-quinazolines substituted at position 2 of the quinazoline ring with a variety of N-methylaminoalkyl residues, among which the N-methyl-diphenyl-4,4-n-butylamino group (FR-A-2,389,614), or with hydroxyacyl groups, such as the 4-(2hydroxy-2-phenylacetyl)piperazin-1-yl group (EP-A-225,866).

It was now founded, and it is an object of the present invention, that modifying the substituents of the piperazine-ring new derivatives are obtained showing a good affinity for the α₁-adrenoreceptors and lower toxicity when compared with the known compounds.

The compounds according to the present invention have general formula (I)

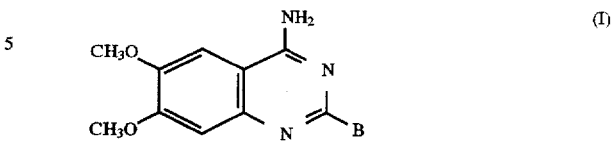

wherein B represent one of the following groups:

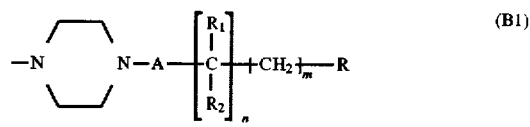

wherein:

A is chosen in the group of: a chemical bond, —CO—, —CONH—, each of them being represented in order to show that the left side is the part linked to the heterocyclic ring and the right side is linked to the alkyl-chain;

$R_1$ and $R_2$, same or different, represent independently from each other an hydrogen atom, linear or branched alkyl-group having from 1 to 4 carbon atoms;

n is 0 or 1;

m is comprised between 0 and 4 and

R represents a group: aryl, diarylmethyl, aroyl, aryl (hydroxy)methyl, alkyloxycarbonyl, aryloxy unsubstituted or possibly substituted with one or more of the groups: alcoxy, branched or linear alkyl having from 1 to 4 carbon atoms, or —CONHR$_3$ or —N(R$_4$)R$_5^-$ wherein:

$R_3$ is H, linear or branched alkyl having from 1 to 4 carbon atoms, aryl;

$R_4$ and $R_5$, same or different, represent independently from each other: H, linear or branched alkyl having from 1 to 4 carbon atoms, benzyloxycarbonyl, methanesulfonyl, benzyloxycarbonylglycinoyl:

wherein

Alk represents alkyl having 1 to 3 carbon atoms and

Z is a phenyl, benzidryl or 4(2-methoxyphenyl)-1-piperazinyl;

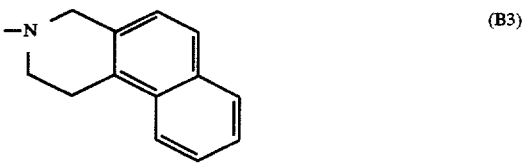

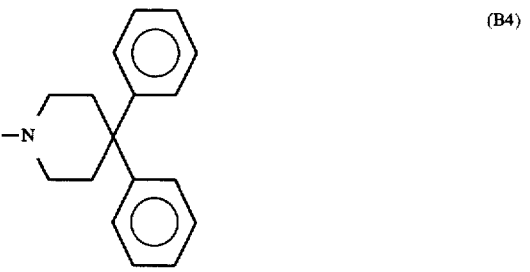

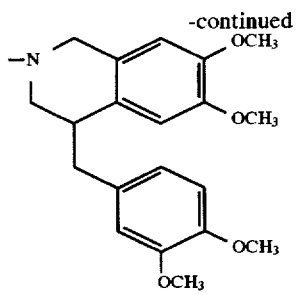 (B5)

The inventions includes also the enantiomers, the diastereoisomers, N-oxydes and the addition salts of these compounds with pharmaceutically acceptable acids.

Preferred compounds according to the present invention are in particular those reported in dependent claims.

The compounds of the invention were tested in order to show their interest as substances having a potentially therapeutic activity. In particular the antagonistic activity on $\alpha_1$-adrenoreceptors was determined and it was proved that the activity is present both "in vivo" and "in vitro". The toxicity-tests suggested a minor presence of undesired side effects.

Moreover, for some compounds according to the invention a good selectivity for the subline $\alpha_{1B}$-adrenergic in respect to the sublines $\alpha_{1A}$ and $\alpha_{1D}$.

The above reported results confirm the potential use of such compounds in the treatment of disorders related to an hyperactivity of the $\alpha$-adrenergic system as, for example arterial hypertension, prostate benign hyperplasia, hugh intraocular pressure and hypercholesterolemia.

Therefore a further aspect of the present invention is represented by pharmaceutical compositions wherein the active principle is a compound of formula (I), or an enantiomer, a diastereoisomer, N-oxyde or pharmaceutically acceptable salts thereof, in combination with pharmaceutically acceptable excipients, eluents or carriers.

Synthesis of the compounds according to the invention

Generally the compounds of formula I can be prepared by condensing 2-haloquinazoline of formula II:

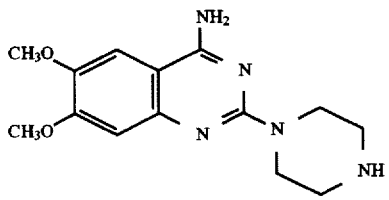 (II)

wherein X is an halogen atom, with amino-derivatives of formula III:

BH    (III)

wherein B is anyone of the above said groups $B_1$–$B_5$ as above defined excluded the case of $B_1$ when R is the group —N(R$_4$)R$_5$ wherein R$_4$ and R$_5$ are, both or independently, H or alkyl.

The above said condensation can be performed in polar solvents having high boiling point (for example isoamylalcohol, DMF) at 120° C./under reflux as shown in Examples 1, 2, 21, 22 and 28–33.

The compounds wherein B represents the group $B_1$ can also be prepared by condensation of the quinazoline-derivative of formula IV:

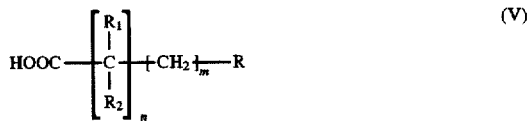 (IV)

with carboxylic acids of formula V:

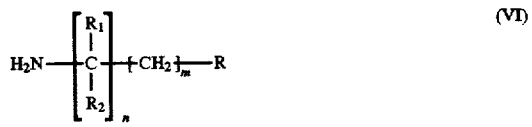 (V)

wherein R, R$_1$, R$_2$, n and m are as above defined or with reactive derivatives of such acids as for example the corresponding chlorides. The above said condensations are performed in the presence of a condensing agent (for example N,N'-dicyclohexylcarbodiimide) and a promoting agent (for example 4-dimethylaminopyridine) in an aprotic and/or chlorinated solvent (for example DMF, CHCl$_3$) at 0°/+140° C. as shown in the Examples 3–6, 11–13, 15, 17, 18 and 23–27. When reactive derivatives of the acids are used, the reactions are performed at 0°/+80° C. in the presence of a tertiary-amine (for example triethylamine) or other acceptor of the formed acid.

Another method of preparation, shown in Example 10, is the reaction of the quinazoline derivative of formula IV with amines of formula VI:

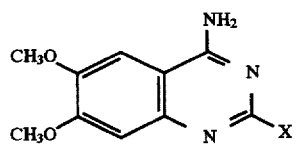 (VI)

wherein R, R$_1$, R$_2$, n and m are as above defined, in the presence of N,N'-carbonyldiimidazole in an aprotic solvent (for example tetrahydrofuran) at 0°/+50° C.

The compounds wherein R represents an aryl(hydroxy) methyl-group can be prepared by reduction of the corresponding aroyl-derivatives with reducing agents (for example sodium borohydrure) in protic solvents (for example water or methanole) at 0°/+40° C. (Examples 14 and 16).

The compounds wherein R is a —N(R$_4$)R$_5$ group, wherein R$_4$ and R$_5$ are H respectively, can be prepared by hydrolisys of the corresponding compounds wherein R$_4$ or R$_5$ are the group COOCH$_2$C$_6$H$_5$.

Such reactions, shown in the Examples 7 or 8, are performed in protic solvents (for example acetic acid) in the presence of a strong acid (for example bromidric acid) at 0°/+40° C. as described by T. W. Greene, Protective Groups in Organic Synthesis, p. 335, Wiley Interscience (1991) or according to other methods therein described.

The compounds wherein R is a group —N(R$_4$)R$_5$, wherein R$_4$ and R$_5$ are respectively H and a methanesulfonyl group, can be prepared by acylation with methanesulfonylchloride of the corresponding compounds wherein R$_4$=R$_5$=H. The reaction (Example 9) is performed in aprotic solvents (for example pyridine) in the presence of a base (for example triethylamine) at 0°/+40° C.

Detailed preparation of the intermediates
1-(2-Phenoxy-2-methylpropionyl)piperazine hydrochloride (Intermediate I)

To a solution of 17.2 g of anhydrous piperazine in 50 ml of EtOH 95% and 22 ml of H$_2$O, 3.37 g of HBr 48% are dropped in about 10' and thereafter, in about 40' and at room temperature, a solution of 9.93 g of 2-phenoxy-2-methylpropionyl chloride (prepared according to: Bull. Soc. Chim. Fr. 1956, 776–783) in 70 ml of THF. The suspension is stirred 2 h at the same temperature and 3 h under reflux, diluted with 130 ml of THF, cooled, and the piperazine salts precipitated are filtered away. The filtered is evaporated to dryness, the residue is resuspended with 120 ml of $H_2O$ and 35 ml HCl 2N and extracted with $Et_2O$; the aqueous phase is treated with 40 ml NaOH conc. and extracted with $Et_2O$ (4×50 ml). The ethere-phase, dried, is treated with HCl in $Et_2O$ about 3N and the precipitate is collected by filtration and crystallized from EtOH giving 5.98 g (42%) of the wanted compound; m.p.: 236°–238° C.

1-[2-Methyl-2-(2-methoxyphenoxy)propionyl]piperazine hydrochloride hydrated
(Intermediate II)

To a boiling solution of 10.5 g of 2-(2-methoxy-phenoxy)-2-methylpropionic acid, prepared according to: Gazz. Chim. It. 93, 335–338 (1963), in 50 ml of anhydrous $CHCl_3$ a solution of 5.4 ml of $SOCl_2$ in 20 ml of anhydrous $CHCl_3$ is dropped in about 30' and the solution is refluxed for 2 h. The residue obtained by evaporation to dryness of the solvent is used, instead of 2-phenoxy-2-methyl-propionyl chloride, to prepare the wanted compounds according to the method described for the Intermediate I. After crystallization from methyl-ethylchetone 6.3 g (34%) of Intermediate II are obtained; m.p. 95°–98° C.

2-Methoxy-6-isopropylphenoxyacetic acid
Intermediate III

To a mixture of: 20 g of NaOh in drops, 30 ml $H_2O$, 1.1 g triethylbenzylammonium chloride, 8.4 g 2-isopropyl-6-methoxyphenole (prepared according to: Tetr. Lett. 38, 1397–1404 (1982)) and 40 ml toluene, a solution of 11.1 ml of ethyle bromoacetate in 10 ml toluene is dropped at room temperature in about 15'. The mixture is stirred vigorously at the same temperature for 2 h and thereafter for 2 h at 60°–65° C. and for 6.5 h under reflux, during this last step a solution of 6 ml of ethyle broacetate in 10 ml of toluene is added. At the end the mixture is diluted with 250 ml $H_2O$, the aqueous phase is separated and treated with HCl conc.; the emulsified precipitate is extracted with $Et_2O$ (3×50 ml) and the organic phase is washed with water. Another extraction is performed with 40 ml $Na_2CO_3$ at 20% or the slightly alcaline solution is treated with HCl conc. and extracted with $Et_2O$ (3×40 ml). The ether extracts are pooled and the solvent is evaporated giving 8 g (72%) of the wanted compound; b.p.: 190° C./0.7 mmHg.

2-(2-methoxy-6-isopropylphenoxy)propionic acid.
(Intermediate IV)

This compound is prepared as described according to the method given for Intermediate III but using ethyle 2-bromopropionate instead of ethyle bromoacetate. The wanted compound is isolated (yield 81%) and b.p.: 165°–170° C./0.7 mmHg.

Detailed preparation of the final compounds

EXAMPLE 1
4-Amino-6,7-dimethoxy-2-(4-benzyl-1-piperazinyl)-guinazoline bihydrochloride hemihydrate A mixture of 4.8 g of 4-amino-2-chloro-6,7-dimethoxyquinazoline (prepared according to: J. Med. Chem. 20, 146–149 (1977)) and 4.2 g of N-benzylpiperazine 95% in 120 ml of isoamylic alcohol is stirred under reflux for 4 h and thereafter cooled. The precipitate is collected by filtration and suspended in 150 ml of water and 150 ml $CHCl_3$ and the mixture is treated with NaOH 30%. The organic phase is separated while the aqueous phase is once more extracted with $CHCl_3$ (2×50 ml); the organic extracts are pooled, washed with $H_2O$ (2×30 ml), dryed on anhydrous $Na_2SO_4$ and the solvent is eliminated. The residue is purified by flash-chromatography on $SiO_2$ column eluting with $CHCl_3$/MeOH 100:3 and the fractions containing the pure base are pooled and evaporated to dryness. The residue is dissolved in EtOH and the solution treated with HCl 4N in EtOH up to complete precipitation of the salt which is collected by filtration and crystallized from MeCN/$H_2O$ 7:3 giving 2.6 g (56%) of the wanted compound; m.p.: 265°–267° C.

EXAMPLE 2
4-Amino-6,7-dimethoxy-2-(4-diphenylmethyl-1-piperazinyl)-guinazoline bihydrochloride emihydrate The compound is prepared according to Example 1, but using N-diphenylmethylpiperazine (prepared according to: J. Am. Chem. Soc. 71, 2731–2734 (1949)) instead of N-benzylpiperazine and warming under reflux for 8 h. The crude compound, collected by filtration, is crystallized from EtOH 95%, dissolved in MeOH, added with HCl dil. and the solution is evaporated to dryness. The residue is boiled with $H_2O$ giving the wanted compound. Yield: 56%, m.p.: 273°–274° C.

EXAMPLE 3
4-Amino-6,7-dimethoxy-2-[4-(2,2-diphenylacetyl)-1-piperazinyl]-quinazoline hydrochloride . 0.75 $H_2O$ 2.9 g of 4-amino-6,7-dimethoxy-2-(1-piperazinyl)-quinazoline (prepared according to: J. Med. Chem. 20, 146–149 (1977)) are added in little portions, in about 10' and at room temperature, to a solution of 4.2 g dicyclohexylcarbodiimide 97% and 0.12 g of 4-dimethylaminopyridine in 60 ml $CHCl_3$. The mixture is stirred for 10' at the same temperature and added with 2.55 g of 2.2-diphenylacetic acid and again stirred for 6 h. The residue obtained after evaporation of the solvent is purified by flash chromatography on $SiO_2$ column elating with $CHCl_3$/MeOH 100:2. The fractions containing the pure base are pooled, the solvents evaporated, the residue is dissolved in warm EtOH 95% and the solution treated with HCl in EtOH about 4N. The salt which crystallizes by cooling the solution is collected by filtration and recrystallized from EtOH 90% to give 3.2 g (60%) of the wanted compound; m.p.: 282°–283° C.

EXAMPLE 4
4-Amino-6,7-dimethoxy-2-[4-(3,3-diphenylpropionyl)-1-piperazinyl]-guinazoline hydrochloride
Method a)

A solution of 7.92 g of 3.3-diphenylpropionic acid in 10 ml of anhydrous DMF is dropped, in about 15' and at room temperature, in a suspension of 5.8 g of 4-amino-6,7-dimethoxy-2-(1-piperazinyl)quinazoline, 8.42 g of cyclohexylcarbodiimide 97% and 0.37 g of 4-dimethylaminopiridine in 20 ml of anhydrous DMF. The clear olution so obtained is stirred at the same temperature for 5 h and a precipitated is formed (dicyclohexylurea) which is filtered away. The solvent is evaporated to dryness under vacuum and the resulting vetrous residue is filtered after treating with 500 ml $Et_2O$. The crude compound is purified by flash chromatography on $SiO_2$ column eluting with $CHCl_3$/MeOH 100:2. The fractions containing the pure base are pooled, the solvents evaporated to dryness, the residue suspended in warm EtOH and the suspension is treated with HCl in EtOH about 4N up to complete solution.

After cooling the crystallized salt is collected by filtration and recrystallized from MeCN/$H_2O$ 8:2 giving 5.9 g (55%) of the wanted product; m.p.: 239°–240° C.

Method b)

A solution of 4.4 g of 3,3-diphenylpropionyl chloride (prepared according: Coll. Czech. Chem. Commun. 25, 736–742 (1960) [CA 54, 13055h (1960)] in 30 ml of CHCl$_3$ free from EtOH is dropped at room temperature, in about 15', in a solution of 5.2 g of 4-amino-6,7-dimethoxy-2-(1-piperazinyl)-quinazoline and 2.8 ml di Et$_3$N in 50 ml of anhydrous DMF. The mixture is stirred at the same temperature for 6 h, the solvents evaporated to dryness under vacuum, the residue dissolved in 150 ml CHCl$_3$ and the solution washed with NaHCO$_3$ 2.5% and H$_2$O and thereafter dried on anhydrous Na$_2$SO$_4$. The process is continued as above described for method a) and 4.3 g (43%) of the wanted compound are obtained.

EXAMPLE 5

4 - A m i n o - 6 , 7 - d i m e t h o x y - 2 - { 4 - [ ( 3 - benzyloxycarbonylamino) propionyl]-1-piperazinyl}-quinazoline hydrochloride emihydrate This compound is prepared according to Example 3 but 3-(benzyloxycarbonylamino)propionic acid is used instead of 2,2-diphenylacetic acid and stirring maintained for 5 h. The purification of the crude compound is performed by flash chromatography on SiO$_2$ column eluting with CH$_2$Cl$_2$/MeOH 100:5. The wanted compound is crystallized from EtOH 99%. Yield: 63%, m.p.: 166°–168° C.

EXAMPLE 6

4 - A m i n o - 6 , 7 - d i m e t h o x y - 2 - { 4 - [ ( 4 - benzyloxycarbonylamino) butirryl]-1-piperazinyl}-quinazoline hydrochloride . 1.5 H$_2$O This compound is prepared as described in Example 5, using 4-(benzyloxycarbonylamino)butirric acid instead of 3-(benzyloxycarbonylamino)propionic acid. The wanted compound is crystallized from EtOH and melts at 160°–169° C. Yield 83%.

EXAMPLE 7

4-Amino-6,7-dimethoxy-2-[4-(3-aminopropionyl)-1-piperazinyl]-guinazoline dihydrobromide . 1.75 H$_2$O 20 ml of a solution of HBr 30% in AcOH is dropped, in about 10', in a solution of 4.95 g of the compound prepared in Example 5 in the form of base (prepared according to known methods) in 20 ml of AcOH. The mixture is stirred at the same temperature for 2 h and thereafter diluted with 800 ml Et$_2$O. The precipitate which is collected by filtration is crystallized from EtOH/H$_2$O 4.5:1 giving 4.7 g (85%) of the wanted compound; m.p.: 217° C.

EXAMPLE 8

4-Amino-6,7-dimethoxy-2-[4-(4-aminobutirryl)-1-piperazinyl]-guinazoline dihydrobromide . 0.25 H$_2$O This compounds is prepared according to the Example 7 but using the compound prepared in Example 6 in the form of its base (prepared according to known methods). The crude compound is crystallized from MeOH and melts at 272°–274° C. Yield: 84%.

EXAMPLE 9

4-Amino-6,7-dimethoxy-2-{4-[(4-methylsulfonylamino) butirry]-1-piperazinyl}-quinazoline hydrochloride To a suspension of 5.3 g of the compound prepared in Example 8 in 50 ml anhydrous piridine 5.6 ml of Et$_3$N are dropped at room temperature and, after 15', 2 ml of methanesulfonylchloride are added at the same temperature and in about 10'. After 1 h stirring, the mixture is poured in 700 ml Et$_2$O and the precipitate, collected by filtration, is solved in 250 ml of H$_2$O and the solution added with sodium carbonate. The crude base is extracted with chloroform and the residue, obtained by evaporation of the solvent, is filtered after treatment with 250 ml Et$_2$O. The solid is purified by flash chromatography on SiO$_2$ column eluting in a CH$_2$Cl$_2$/MeOH gradient from 100:5 to 100:10. The fractions containing the pure base are pooled, the solvents evaporated and the residue suspended in warm EtOH 99%; the addition of HCl 4N in EtOH gives a clear solution from which, by cooling, the hydrochloride crystallizes. Another crystallization from EtOH 95% gives 2.1 g (43%) of the wanted compound: m.p.: 231°–233° C.

EXAMPLE 10

4-Amino-6,7-dimethoxy-2-{4-[(2-dimethylaminoethyl) amino-carbonyl]-1-piperazinyl}-quinazoline dihydrochloride tetrahydrate To a suspension of 4.52 g of N,N'-carbonyldiimidazole in 30 ml anhydrous THF a solution of 2.48 g of N,N-dimethylethylendiamine 97% in 10 ml anhydrous THF is dropped and, after 15' stirring at room temperature, a solution of 5.8 g of 4-amino-6,7-dimethoxy-2-(1-piperazinyl) quinazoline in 250 ml anhydrous CHCl$_3$ is dropped therein in about 15'. The mixture is stirred at the same temperature for 24 h, added with 2.3 g of N,N'-carbonylimidazole and stirred for 48 h, thereafter the solvents are evaporated to dryness. The oily residue is purified by flash chromatography on SiO$_2$ column eluting with CHCl$_3$/NH$_3$ 3N in MeOH 100:10 and thereafter on Al$_2$O$_3$ column eluting with CHCl$_3$/MeOH 100:10. The fractions containing the pure product are pooled, the solvents evaporated, the residue solved in EtOH and the solution treated with HCl 4N in EtOH. The solution is evaporated to dryness and the crude hydrochloride is crystallized from EtOH-AcOEt 2:1 to give 5.5 g (50%) of the wanted compound; m.p.: 206°–210° C.

EXAMPLE 11

4 - A m i n o - 6 , 7 - d i m e t h o x y - 2 - { 4 - [ 2 - (benzyloxycarbonylamino)-acetyl]-1-piperazinyl}-quinazoline hydrochloride This compound is prepared as described in Example 5 but using N-benzyloxycarbonylglycine instead of 3-(benzyloxycarbonylamino)propionic acid and stirring the mixture for 7 h.

The purification of the crude compound is made by flash chromatography on SiO$_2$ column eluting with a mixture of CHCl$_3$/MeOH 100:3. The wanted compound is crystallized from EtOH/H$_2$O 2:1. Yield: 79%: m.p.: 263°–265° C.

EXAMPLE 12

4 - A m i n o - 6 , 7 - d i m e t h o x y - 2 - { 4 - [ 2 - [ 2 - (benzyloxycarbonylamino)-acetylamino]acetyl]-1-piperazinyl}-quinazoline hydrochloride hemihydrate This compound is prepared according to Example 5 but using N-benzyloxycarbonylaminoacetylglycine instead of 3-(benzyloxycarbonylamino)propionic acid and DMF as reaction solvent. The crude compound is purified by flash chromatography on SiO$_2$ column eluting with a mixture of CHCl$_3$/MeOH 100:5. The wanted compound is crystallized from EtOH/H$_2$O 2:1. Yield: 60%; m.p.: 246°–248° C.

EXAMPLE 13

4-Amino-6,7-dimethoxy-2-[4-(2-benzoylacetyl)-1-piperazinyl]-quinazoline

This compound is prepared according to Example 5 but using benzoylacetic acid instead of 3-(benzyloxycarbonylamino)propionic acid. The crude compound is purified by flash chromatography on SiO$_2$ column eluting with a mixture of CH$_2$Cl$_2$/MeOH 100:3. The wanted compound is crystallized from CH₃CN. Yield: 60%; m.p.: 214°–215° C.

EXAMPLE 14

4-Amino-6,7-dimethoxy-2-[4-(3-hydroxy-3-phenylpropionyl)-1-piperazinyl]-quinazoline To a suspension of 3 g of the compound prepared in Example 13 in 50 ml MeOH a solution of 0.43 g of NaBH₄ 96% in 4 ml iced H₂O containing 0.2 ml NaOH 30% is quickly added and the mixture is stirred at room temperature for 8 h. Thereafter 2 g (5×0.4) of NaBH₄ are added in 8 h. The suspension is diluted with 10 ml acetone, treated with diluted HCl, neutralized with sodium bicarbonate in 5% solution and concentrated under vacuum. The aqueous suspension is diluted with H₂O and extracted with CHCl₃; the organic phase is washed with H₂O, dried on anhydrous Na₂SO₄ and the residue, obtained by evaporation of the solvent, is purified by flash chromatography on SiO₂ column eluting with CH₂Cl₂/MeOH 100:5. The crude compound, obtained after pooling the pure fractions and evaporating the solvent, is crystallized from EtOH giving 2.34 g (79%) of the wanted compound; m.p.: 222° C.

EXAMPLE 15

4-Amino-6,7-dimethoxy-2-{4-[(3-benzoyl)propionyl]-1-piperazinyl}-quinazoline hydrochloride hydrate This compound is prepared according to Example 5 but 3-benzoylpropionic acid is used instead of 3-(benzyloxycarbonylamino)propionic acid. The crude product is purified by flash chromatography on SiO₂ column eluting with CHCl₃/MeOH 100:3. The wanted compound is crystallized from CH₃CN/H₂O 63:35 and melts at a temperature >270° C. Yield: 62%.

EXAMPLE 16

4-Amino-6,7-dimethoxy-2-[4-(4-phenyl-4-hydroxybutirryl)-1-piperazinyl]-quinazoline maleate (1:1)

This compound is prepared according to Example 14 but the compound prepared in Example 15 is used instead of the one prepared in Example 13. The crude product is purified eluting the column with CH₂Cl₂/MeOH 100:10. The wanted compound is obtained with a yield of 67% after crystallization from EtOH; m.p.: 204°–206° C.

EXAMPLE 17

4-Amino-6,7-dimethoxy-2-[4-(3-oxo-3-aminopropionyl)-1-piperazinyl]-quinazoline hydrochloride hydrate This compound is prepared as described in Example 5 but 3-oxo-3-aminopropionic acid is used instead of 3-(benzyloxycarbonylamino)propionic acid and as reaction solvent the anhydrous mixture CHCl₃/DMF 6:4 is used. The mixture is stirred at room temperature for 96 h during which is added, in portion, with 2 equivalents of 3-oxo-3-aminopropionic acid and 2.5 equivalents of N,N'-dicyclohexylcarbodiimide. Purification of the crude product is performed by flash chromatography on SiO₂ column in CH₂Cl₂/MeOH gradient from 100:20 to 100:50. The wanted compound is crystallized from EtOH 88%. Yield: 23%; m.p.: 241°–243° C.

EXAMPLE 18

4-Amino-6,7-dimethoxy-2-[4-(2-ethoxycarbonylacetyl)-1-piperazinyl]-quinazoline hydrochloride This compound is prepared as described in Example 5 but monoethylester of malonic acid is used instead of 3-(benzyloxycarbonylamino)propionic acid and as reaction solvent, DMF instead of CHCl₃ is used for 3 h at room temperature. Purification of the crude product is performed by flash chromatography on SiO₂ column eluting with CH₂Cl₂/MeOH 100:3. The wanted compound is crystallized from EtOH 80%. Yield: 60%; m.p.: 249°–250° C.

EXAMPLE 19

4-Amino-6,7-dimethoxy-2-[4-(3-n-butylamino-3-oxopropionyl)-1-piperazinyl]-quinazoline hydrochloride A mixture of 4 g of the compound prepared in Example 18 and 30 ml of n-butylamine in 10 ml DMSO is warmed at 140° C. for 20 h in a closed flask. The solution is evaporated under vacuum, the oily residue is treated with 200 ml H₂O and extracted with CHCl₃ (3×50 ml). The vitrous residue, obtained by evaporating the organic phase, is dissolved in 40 ml EtOH 95%, the solution is added with 10 ml KOH 0.3N and warmed to reflux for 30'. The residue obtained by evaporation of the solution is purified by flash chromatography on SiO₂ column eluting with a CHCl₃/MeOH gradient from 100:3 to 100:10. The crude product, obtained by evaporating the fractions containing the pure compound, is dissolved in 75 ml EtOH, the solution acidified with HCl in EtOH 4N and the hydrochloride is collected by filtration, crystallized from EtOH 90% giving 2.5 g (53%) of the wanted compound; m.p.: 260°–262° C.

EXAMPLE 20

4-Amino-6,7-dimethoxy-2-[4-(phenylaminocarbonylacetyl)-1-piperazinyl]-quinazoline hydrochloride hemihydrate A mixture of 4 g of the compound obtained in Example 18 and 14 ml aniline in 6 ml DMF is warmed at 155° C. for 5.5 h.

The obtained product is purified as described in Example 19 by eluting with CHCl₃/MeOH gradient from 100:3 to 100:4. The crude hydrochloride is crystallized from DMF/H₂O 1:1 to give 1.54 g (31%) of the wanted compound; m.p.: >270° C.

EXAMPLE 21

4-Amino-6,7-dimethoxy-2-[4-(2-phenoxy-2-methylpropionyl)-1-piperazinyl]-quinazoline hydrochloride . 1.5 H₂O This compound is prepared according to Example 2 but the intemediate I is used instead of N-diphenylmethylpiperazine and reflux maintained for 3 h. The precipitate is filtered and crystallized from isopropanole to give the wanted compound. Yield 78%; m.p.: 264° C.

EXAMPLE 22

4-Amino-6,7-dimethoxy-2-{4-[2-(2-methoxyphenoxy)-2-methylpropionyl]-1-piperazinyl}-quinazoline hydrochloride This compound is prepared as described in Example 1 but intermediate II is used instead of N-benzylpiperazine, refluxing for 5 h and using a AcOEt/MeOH gradient from 100:0 to 100:10 as eluting mixture. The wanted compound is crystallized from EtOH 80%. Yield: 57%; m.p.: 288° C. (dec.).

EXAMPLE 23

4-Amino-6,7-dimethoxy-2-[4-(2-methoxyphenoxyacetyl)-1-piperazinyl]-quinazoline hydrochloride This compound is prepared as described in Example 3 but 2-methoxyphenoxyacetic acid is used instead of 2,2-diphenylacetic acid and stirring maintained for 5 h. The residue, obtained after column purification, is crystallized from dioxane, suspended in EtOH 85% and acified with HCl about 4N in EtOH. The hydrochloride, collected by filtration, is crystallized from H₂O/DMF 2:1 to give the wanted compound. Yield 61%; m.p.: 263°–265° C.

EXAMPLE 24

4-Amino-6,7-dimethoxy-2-{4-[(2-methoxy-6-isopropylphenoxy)acetyl]-1-piperazinyl}-quinazoline hydrochloride To a boiling solution of 6 g of intermediate III in 30 ml $CCl_4$ 3.6 ml of $SOCl_2$ are dropped and the mixture is stirred under reflux for 2 h. The oily residue, obtained by evaporation of the reaction mixture, is reacted with 4-amino-6,7-dimethoxy-2-(1-piperazinil)quinazoline instead of 3,3-diphenylpropionyl chloride in order to obtain the wanted compound as described in Example 4 (Method b), stirring for 2 h. The purification is performed by column chromatography using $CHCl_3$/MeOH 100:3 as eluting mixture. The wanted compound is crystallized from EtOH. Yield: 45%; m.p.: 252°–254° C.

EXAMPLE 25
4-Amino-6,7-dimethoxy-2-{4-[(2-isopropyl-5-methylphenoxy)acetyl]-1-piperazinyl}-quinazoline hydrochloride . 0.25 $H_2O$ This compound is prepared according to Example 5 but 2-isopropyl-5-methylphenoxyacetic acid (prepared according to: Cesk. Farm. 17, 28–33 (1968) [CA 69, 67041g (1968)]) is used instead of 2,2-diphenylacetic acid and stirring maintained for 5 h. The wanted compound is crystallized from EtOH 95%. Yield: 80%; m.p.: 251°–253° C.

EXAMPLE 26
4-Amino-6,7-dimethoxy-2-{4-[2-(2-methoxy-6-isopropylphenoxy)propionyl]-1-piperazinyl}-quinazoline hydrochloride To a boiling solution of 4.8 g of the intermediate IV in 25 ml $CCl_4$ 3 ml of $SOCl_2$ are dropped in about 15' and the mixture is refluxed for 3 h. The oily residue, obtained by evaporating the rection mixture, is used instead of 3,3-diphenylpropionyl chloride, stirring for 2 h in order to obtain the wanted compound as described in Example 4 (Method b). The compound is purified as described in Example 25 and the wanted compound is crystallized from EtOH. Yield: 58%; m.p.: 227°–229° C.

EXAMPLE 27
4-Amino-6,7-dimethoxy-2-[4-(2,6-dimethoxyphenoxy)acetyl-1-piperazinyl]-quinazoline hydrochloride . 0.25 $H_2O$ This compound is prepared according to Example 5 but 2,6-dimethoxyphenoxyacetic acid (prepared according to GB-679,676) is used instead of 2,2-diphenylacetic acid and using $CHCl_3$/MeOH 100:1 as column eluting mixture. The wanted compound is crystallized from EtOH 95% and thereafter from DMF. Yield: 21%; m.p.: 258°–260° C. (dec).

EXAMPLE 28
4-Amino-6,7-dimethoxy-2-(N-benzyl-N-methylamino)-guinazoline hydrochloride This compound is prepared according to Example 1 but N-meyhylbenzylamine is used instead of N-benzylpiperazine and reflux maintained for 7 h. The crude base is purified by crystallization from EtOH, then dissolved in boiling EtOH and the solution is added with HCl about 4N in EtOH. The wanted compound is obtained with a yield: 62%; m.p.: 261°–262° C.

EXAMPLE 29
4-Amino-6,7-dimethoxy-2-(N-methyl-3,3-diphenylpropylamino)-guinazoline hydrochloride This compound is obtained according to Example 1 but N-methyl-3,3-diphenylpropylamine (prepared according to DE-925,468) is used instead of N-benzylpiperazine and reflux maintained 12 h. The purification of the crude base is performed by flash chromatography on $SiO_2$ column using as eluents $CHCl_3$/MeOH 100:2. The wanted compound is crystallized from EtOH 95%. Yield 29%; m.p.: 258°–259° C.

EXAMPLE 30
4-Amino-6,7-dimethoxy-2-(1,2,3,4-tetrahydrobenzo[f]isoquinolin-2-yl)-quinazoline . 0.25 ethanole This compound is prepared according to Example 1 but using 1,2,3,4-tetrahydrobenzo[f]isoquinoline (prepared according to Indian J. Chem. 1974, 113–116) instead of N-benzylpiperazine and refluxing 9 h in the darkness and under nitrogen. The purification is performed by flash chromatography on $SiO_2$ column eluting with $CH_2Cl_2$/$NH_3$-MeOH 5N gradient from 100:0.5 to 100:1.5. The wanted compound is crystallized from EtOH 99%. Yield: 30%; m.p.: 177°–180° C. (dec)

EXAMPLE 31
4-Amino-6,7-dimethoxy-2-{N-methyl-N-{3-[4-(2-methoxyphenyl)-1-piperazinyl]propyl}amino}-quinazoline dihydrochloride dihydrate This compound is prepared as described in Example 1 but using N-methyl-3-[4-(2-methoxyphenyl)-1-piperazinyl]-propylamine (prepared according to DE-2,143,730) instead of N-benzylpiperazine and refluxing 12 h. The crude base is purified by flash chromatography on $SiO_2$ column eluting with $CHCl_3$/$NH_3$-MeOH about 2N 100:3. The wanted compound is crystallized from EtOH 92%. Yield: 60%; m.p.: 208°–210° C.

EXAMPLE 32
4-Amino-6,7-dimethoxy-2-(4,4-diphenyl-1-piperidinyl)-guinazoline hydrochloride . 0.65 $H_2O$ This compound is prepared as described in Example 1 but 4,4-diphenylpiperidine [prepared according to Arzneim.-Forsch. 34, 233–240 (1984)] instead of N-benzylpiperazine and refluxing for 8 h. The crude base is purified by crystallization from DMF-$H_2O$ (3:1). The wanted compound is crystallized from DMF-$H_2O$ (1:1). Yield 61%; m.p.: >290° C.

EXAMPLE 33
4-Amino-6,7-dimethoxy-2-[1-(3,4-dimethoxybenzyl)-6,7-dimethoxy-1,2,3,4-tetrahydroisoguinolin-2-yl]-quinazoline hydrochloride hydrate A mixture of 3.6 g of 4-amino-2-chloro-6,7-dimethoxyquinazoline, 5.15 g 1,2,3,4-tetrahydropapaverine (prepared according to Eur. J. Med. Chem. - Chim. Ther. 9, 233–238 (1974)), 2.16 g potassium iodide and 15 ml anhydrous DMF is warmed under stirring at 120°–125° C. for 8 h. The mixture is poured in 400 ml $H_2O$ and the precipitate, collected by filtration, is purified by flash chromatography on $SiO_2$ column eluting with $CHCl_3$/MeOH 100:1 and the fractions containing the pure base are pooled and evaporated to dryness. The residue is dissolved in MeOH and the solution treated with HCl in $Et_2O$ about 3N up to complete precipitation of the salt which is filtered and crystallized from MeOH to give 6.31 g (70%) of the wanted compound; m.p.: 226°–230° C.

PHARMACOLOGICAL DATA

Methodology

Male Sprague Dawley rats (Crl: CD' BR) of 175–300 g b.w., male spontaneously hypertensive rats, Okamoto strain, female Albino Swiss mice [Crl:CD-1 (ICR) BR] 20–30 g b.w., were obtained from Charles River, Italy. Animals were housed with free access to food and water and maintained on forced light-dark cycle at 22°–24° C. until the day of experiments.

Acute toxicity

The acute toxicity of synthesized compounds was evaluated in female Albino Swiss mice after intraperitoneal and oral administration. Four logarithmic scaled doses of the compounds were dissolved or suspended in 0.5% Methocel and administered in a volume of 10 ml/kg to groups of 4 mice/dose. Mortality was recorded 7 days after the administration. Data analysis: the $LD_{50}$ values and their fiducial limits were calculated according to the method of Weil [Biometrics, 8, 249, 1952].

Receptor Binding studies

The following receptor binding studies, as well as the experimental data reported below, establish compounds of the invention as $\alpha_1$-blockers.

[$^3$H]Prazosin binding ($\alpha_1$-receptors)

Rat cerebral cortices were homogenized in 50 volumes of original wet weight of ice-cold 50 mM Tris-HCl buffer pH 7.4. The homogenates were centrifuged at 48,000 × g for 10 minutes, and the pellets were resuspended in the same volume of ice-cold buffer, centrifuged and resuspended two more times. The final pellets obtained were resuspended in 100 vols of 50 mM Tris-HCl buffer (containing 0.1% ascorbic acid and 10 µM pargyline) pH 7.4 and incubated (1 ml/sample) for 30 min at 25° C. with 0.35 nM [$^3$H]prazosin, in absence or presence of 5–10 concentrations of the displacing compound to be tested. Non specific binding was determined in the presence of 2 µM prazosin. The incubations were terminated by rapid filtration through Whatman GF/B, filters using a Brandel cell harvester and the filters were washed with 3×3 ml of ice-cold buffer. The radioactivity retained on the filters was determined by liquid scintillation counting.

Cloned animal $\alpha_1$adrenoceptors

Expression of rat brain $\alpha_{1D}$ (previously $\alpha_{1A/D}$), syrian hamster smooth muscle cell line DDT1 MF-2 1B and bovine brain $\alpha_{1A}$ (previously $\alpha_{1C}$) adrenoceptors transiently in COS-7 cells (modified monkey kidney ephitelial cells) was performed as previously described [S. Cotecchia et al., Proc. Natl. Acad. Sci. U.S.A. 85, 7159, 1988; D. A. Schwinn et al., J. Biol. Chem. 265, 8183, 1990; J. W. Lomasney et al., J. Biol. Chem. 266, 6365, 1991]. COS-7 cells were grown as monolayers in Dulbecco's modified Eagle's medium (DMEM), supplemented with 25 mM glucose, 10% bovine calf serum, 100 units/ml penicillin and 100 µg/ml streptomicyn sulfate.

Transfected cells from colture flask were washed two times with 5 ml phosphate buffered saline (PBS), scraped into 2 ml of 5 mM Tris-HCl, pH 7.4, containing 5 mM EDTA and 10 µM leupeptin, and lysed by sonication. The cell lysates were pelleted at 30000xg for 15 min at 4° C. and washed three times with 10 ml ice-cold 50 mM Tris-HCl, pH 7.4. Membranes were resuspended in 50 mM Tris-HCl, pH 7.4, containing 10 µM pargyline and 0.1% ascorbic acid, quickly frozen and stored at −70° C. until utilized.

Radioligand binding assays

Membranes were incubated in 50 mM Tris-HCl, pH 7.4, containing 10 µM pargyline and 0.1% ascorbic acid, with 0.3–0.6 nM [$^3$H]prazosin in absence or presence of the displacing drug to be tested over the concentration range $10^{-4}$ to $10^{-13}$ M. Incubation volume was 0.22 ml (35, 35 and 70 µg protein/sample for $\alpha_{1B}$, $\alpha_{1A}$ and $\alpha_{1D}$, respectively).

Non-specific binding was determined in presence of 100 µM phentolamine. The reaction mixture was incubated for 30 min at 25° C. and then stopped by the addition of ice cold Tris-HCl buffer and rapid filtration through 0.2% polyethyleneimine pretreated Whatman GF/B fiber filters using Brandel cell harvester. The filters were then washed with 3×3 ml of ice-cold buffer and the radioactivity retained on the filters was counted in 10 ml of Filter Count (Packard) in a liquid scintillation spectrometer with a counting efficacy of 40%.

Data analysis

The inhibition of specific binding of the radioligands by the tested drugs was analyzed to estimate the $IC_{50}$ value by using the non-linear curve-fitting program Allfit [A. De Lean et al., Am. J. Physiol. 235.

Evaluation of the antihypertensive activity in chateterized spontaneously hypertensive rat (SH) chronic awake and of the hypotensive activity in the normotensed anesthethized rat The SH rats are surgically prepared at least 24 hours before the test. The surgical operation was performed under neuroleptoanalgesia or barbituric anesthesia; the right carotid artery was exposed and a chateter suitable in dimensions and material was introduced in the vessel up to the aortic arch. The chateter was linked to the vessel with suitable suture thread and run under the skin up to the animal neck where was brought to the exterior and connected to a "Swivel" which allows free-motion of the animal, inside its cage, during testing. The chateter end was connected to a pressure transductor which send the signal to polygraph pre-amplifier.

For endovenous administrations a second chateter similar to the one above described was introduced during the surgical operation into the left jugular vein and brought to the exterior as the arterious chateter. Both chateters where filled with suitable volumes of eparinated solution, in order to prevent coaugulation or formation of thrombuses, which will prevent the registration of the pressure wave or the endovenously administration of the solution. About 30' before administration the arterious pressure was monitored and the registration of the parameters was performed after administration at different times according to the test protocol.

Normotensed rats with were prepared surgically at the moment of the test, after anesthesia with pentobarbital. Suitable chateters were introduced in the left carotid artery and the right jugular vein. The arterious chateter end was connected to a pressure transductor which sends the signal to a polygraph preamplifier. About 30' before the administration the arterious pressure was monitored and the registration of the parameters was performed after the administration, at various time according to the test protocol.

For the endovenous administration the administered volum was 0.5–1 ml/Kg, while for the oral administration was 5 ml/Kg.

Evaluation of data: in so far as the espression of the results is concerned, the pressure data were reported as percentage of the variation in respect to the base values. Based on these data, at the maximum of the effect, a $DE_{25}$ was evaluated (as the dose which induces a lowering of 25% of the dyastolic arterious pressure) by linear regression log-dose against response.

For example the compound described in Example 13 shows a $DE_{25}$ of 56 µg/Kg following to the endovenous administration in the normotensed rat and a $DE_{25}$ of 2.42 mg/Kg after oral administration in SHR rat.

Results

The compounds prepared in the examples were tested according to the above reported methods and compared with the results obtained with the usual standards.

The results are reported:

In TABLE 1 in connection with the affinity for the $\alpha_1$([$^3$H]prazosine) receptor and their acute toxicity ($DL_{50}$);

in TABLE 2 in connection with the shown affinity for sublines of cloned receptors $\alpha_{1A}$, $\alpha_{1B}$, $\alpha_{1D}$.

TABLE 1

| Example No. | [³H] prazosine IC₅₀ nM | DL₅₀ mg/kg i.p. | DL₅₀ mg/kg p.o. |
|---|---|---|---|
| 1 | 32 | 76 | 301 |
| 2 | 40 | — | — |
| 3 | 5 | 112 | 868 |
| 4 | 3 | 97 | >3000 |
| 5 | 283 | 300 | >3000 |
| 6 | 29 | >1000 | >3000 |
| 7 | 48 | 187 | >3000 |
| 8 | 47 | 219 | >3000 |
| 9 | 86 | >500 | — |
| 10 | 55 | 23 | 1346 |
| 11 | 61 | >1000 | >3000 |
| 12 | 29 | 1132 | >2000 |
| 13 | 7 | 142 | >3000 |
| 14 | 19 | >1000 | >3000 |
| 15 | 15 | >1000 | >3000 |
| 16 | 17 | 253 | >3000 |
| 17 | 105 | — | — |
| 18 | 54 | >1000 | >3000 |
| 19 | 96 | 459 | >2000 |
| 20 | 67 | — | — |
| 21 | 99 | 206 | >1700 |
| 22 | 49 | 435 | >3000 |
| 23 | 17 | 337 | >2000 |
| 24 | 28 | 268 | >3000 |
| 25 | 157 | 346 | >3000 |
| 26 | 123 | 115 | 1957 |
| 27 | 6 | — | — |
| 28 | 70 | 89 | 293 |
| 29 | 85 | 163 | >2000 |
| 30 | 5 | — | — |
| 31 | 12 | 70 | >2000 |
| 32 | 259 | >500 | >2000 |
| 33 | 287 | 884 | >3000 |
| prazosine | 2 | — | 1852 |

TABLE 2

Affinity for the cloned $\alpha_1$-adrenoceptor subtypes
Data represent the IC₅₀ values (nM) and are the mean of 2–4 different experiments, each done in triplicate, which agreed within 10%.

| compound | cloned $\alpha_{1A}$ | cloned $\alpha_{1B}$ | cloned $\alpha_{1D}$ |
|---|---|---|---|
| Example 24 | 17.17 | 1.15 | 22.93 |
| Example 33 | 950.03 | 205.64 | 1549.23 |
| Prazosin | 3.04 | 2.27 | 5.08 |
| Terazosin | 66.63 | 71.95 | 105.63 |

We claim:

1. Compound of general formula (I):

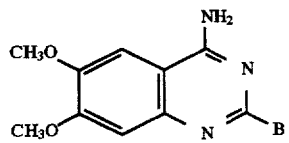

wherein B is one of the following groups:

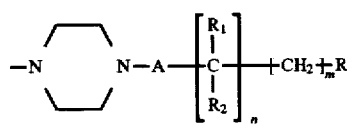
(B1)

wherein:
A is selected from the group consisting of:
a chemical bond and —CO—;

$R_1$ and $R_2$, same or different, represent independently from each other an hydrogen atom or a linear or branched alkyl group having from 1 to 4 carbon atoms;

n is 0 or 1;

m is an integer from 0 to 4 and

R is selected from the group consisting of (i) diphenylmethyl; (ii) benzoyl; (iii) phenoxy substituted with one or more groups selected from the group consisting of alkoxy and branched or linear alkyl having from 1 to 4 carbon atoms; and (iv) —N(R₄)R₅ wherein:

R₄ and R₅, same or different, represent independently from each other: H, linear or branched alkyl having from 1 to 4 carbon atoms, benzyloxycarbonyl, methanesulfonyl, benzyloxycarbonyglycinoyl, provided that when m=n=0, R is different from —NR₄R₅ and benzoyl;

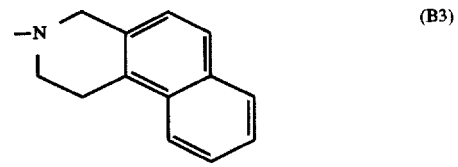
(B3)

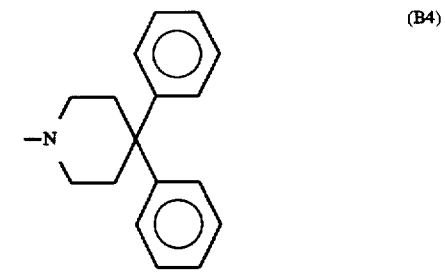
(B4)

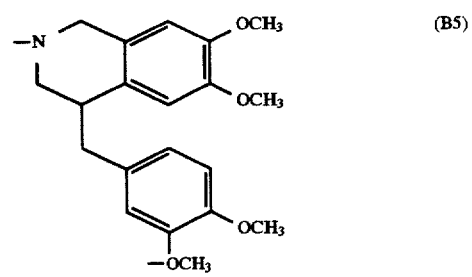
(B5)

or an enantiomer, diastereoisomer, N-oxide, addition salt with a pharmaceutical acceptable acid thereof.

2. A compound as claimed in claim 1, wherein B is (B1) and R is diphenylmethyl.

3. A compound as claimed in claim 2, selected from the group consisting of:
4-Amino-6,7-dimethoxy-2-(4-diphenylmethyl-1-piperazinyl)-quinazoline,
4-Amino-6,7-dimethoxy-2-[4-(2,2-diphenylacetyl)-1-piperazinyl]-quinazoline, and
4-Amino-6,7-dimethoxy-2-[4-(3,3-diphenylpropionyl)-1-piperazinyl]-quinazoline.

4. A compound as claimed in claim 1, wherein B is (B1) and R is NR₄R₅.

5. A compound as claimed in claim 1, wherein B is (B1), A is —CO—, n=0, m is an integer from 0 to 3, R is NR₄R₅, and R₄ and R₅ represent independently from each other: H, linear or branched alkyl having from 1 to 4 carbon atoms, benzyloxycarbonyl, methanesulphonyl, or benzyloxycarbonylglycinoyl.

6. A compound as claimed in claim 4, selected from the group consisting of:

4-Amino-6,7-dimethoxy-2-{4[(3-benzyloxycarbonylamino) propionyl]-1- piperazinyl}-quinazoline, 4-Amino-6,7-dimethoxy-2-{4-[(4-benzyloxycarbonylamino) butyryl]-1-piperazinyl}-quinazoline, 4Amino-6,7-dimethoxy-2-[4-(3-aminopropionyl)-1-piperazinyl]-quinazoline, 4-Amino-6,7-dimethoxy-2-[4-(4-aminobutyryl)-1-piperazinyl]-quinazoline, 4-Amino-6,7-dimethoxy-2-{4-[(4-methylsulfonylamino) butyryl]-1-piperazinyl}-quinazoline, 4-Amino-6,7-dimethoxy-2-{4-[2-(benzyloxycarbonylamino)acetyl]-1-piperazinyl}-quinazoline, and 4-Amino-6,7-dimethoxy-2-{4-[2-[2-(benzyloxycarbonylamino)-acetylamino]acetyl]-1-piperazinyl}-quinazoline.

7. A compound as claimed in claim 1, wherein B is (B1) and R is benzoyl.

8. A compound as claimed in claim 7, selected from the group consisting of:
4-Amino-6,7-dimethoxy-2-[4-(2-benzoylacetyl)-1-piperazinyl]-quinazoline, and
4-Amino-6,7-dimethoxy-2-{4-[(3-benzoyl)propionyl]-1-piperazinyl}-quinazoline.

9. A compound as claimed in claim 1, wherein B is (B1) and R is substituted phenoxy.

10. A compound as claimed in claim 1, wherein B is (B1); A is —CO—; m=0, n=1 and $R_1$ and $R_2$ each independently are H or $CH_3$, or m=1 and n=0, and R is selected from the group consisting of 2-methoxyphenoxy, 2-methoxy-6-isopropylphenoxy, 2-isopropyl-5-methylphenoxy, and 2,6-dimethoxyphenoxy.

11. A compound as claimed in claim 9, selected from the group consisting of:
4-Amino-6,7-dimethoxy-2-{4-[2-(2-methoxyphenoxy)-2-methylpropionyl]-1-piperazinyl}-quinazoline,
4-Amino-6,7-dimethoxy-2-[4-(2-methoxyphenoxyacetyl)-1-piperazinyl]-quinazoline,
4-Amino-6,7-dimethoxy-2-{4-[2-(2-methoxy-6-isopropylphenoxy)acetyl]-1-piperazinyl}-quinazoline,
4-Amino-6,7-dimethoxy-2-{4-[2-isopropyl-5-methylphenoxy)acetyl]-1-piperazinyl}-quinazoline,
4-Amino-6,7-dimethoxy-2-{4-[2-(2-methoxy-6-isopropylphenoxy)propionyl]-1-piperazinyl}-quinazoline, and
4-Amino-6,7-dimethoxy-2-[4-(2,6-dimethoxyphenoxy)acetyl-1-piperazinyl]}-quinazoline.

12. A compound as claimed in claim 1, selected from the group consisting of:
compound of formula (I) wherein B is (B3), corresponding to
4-Amino-6,7-dimethoxy-2-(1,2,3,4-tetrahydrobenzo isoquinolin-2-yl-quinazoline, compound of formula (I) wherein B is (B4), corresponding to
4-Amino-6,7-dimethoxy-2-(4,4-diphenyl-1-piperidinyl)-quinazoline, and compound of formula (I) wherein B is (B5), corresponding to
4-Amino-6,7-dimethoxy-2-[1-(3,4-dimethoxybenzyl)-6,7-dimethoxy-1,2,3,4-tetrahydroisoquinolin-2-yl]-quinazoline.

13. A pharmaceutical composition comprising a therapeutical effective amount of at least one compound according to claim 1, or an enantiomer, a diastereoismoer, N-oxyde or pharmaceutically acceptable salts thereof, in combination with pharmaceutically acceptable excipients, eluents or carriers.

14. A process for the preparation of a compound of general formula (I) as defined in claim 1, comprising condensing a 2-haloquinazoline of formula (II):

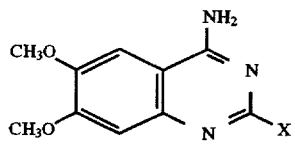

wherein X is

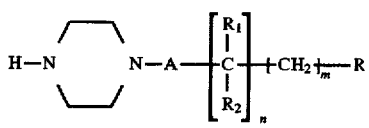

a halogen atom, with amino-derivatives of formula (III)

BH         (III)

wherein BH is selected from the group consisting of B1-H, B3-H, B4-H and B5-H, wherein:
i) B1-H is
wherein A, m, n, R, $R_1$ and $R_2$ are as defined in claim 1, excluded the case of R=N($R_4$)$R_5$, wherein $R_4$ and $R_5$ are both or independently H or alkyl having from 1 to 4 carbon atoms;

ii) B3-H is

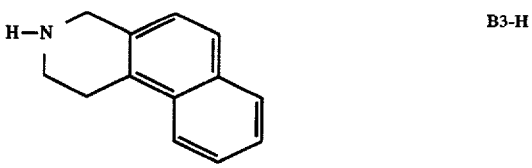

iii) B4-H is

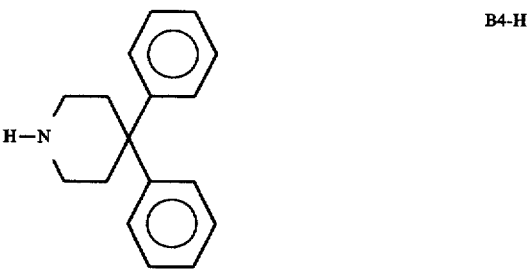

and
iv) B5-H is

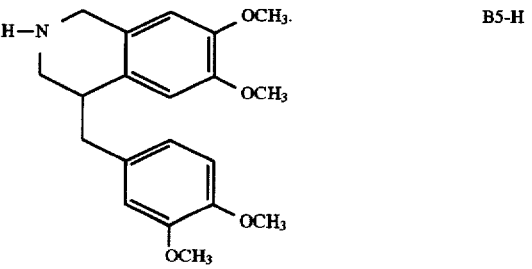

15. The process as claimed in claim 14, carried out in polar solvents having high boiling points, at temperatures comprised between 120° C. and the reflux temperature.

16. A process for the preparation of a compound of formula (I) wherein B is $B_1$ as defined in claim 1, comprising condensing a quinazoline-derivative of formula IV:

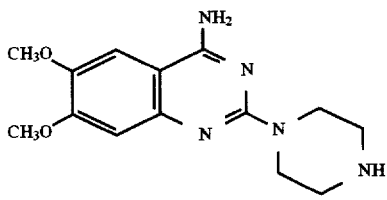

with a carboxylic acid of formula V:

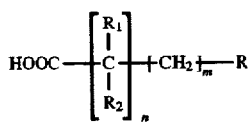

wherein R, $R_1$, $R_2$, n and m are as above defined in claim 1, or with a reactive derivative thereof, in the presence of a condensing agent, and of an acceptor of the formed acid as the promoting agent.

17. The process as claimed in claim 16, wherein the condensing agent is dicycloexylcarbodiimide and the promoting agent is 4-dimethylaminopyridine.

18. The process as claimed in claim 16, carried out in a solvent selected among aprotic and chlorinated solvents.

19. The process as claimed in claim 16, carried out at temperatures comprised between 0° and 140° C.

20. The process as claimed in claim 16, wherein when a reactive derivative of said acid is used, the promoting agent is a tertiary amine and the condensation is carried out at temperatures comprised between 0° and 80° C.

21. A process for the preparation of a compound of formula (I) wherein B is B1 as defined in claim 1, comprising condensing a quinazoline derivative of formula IV

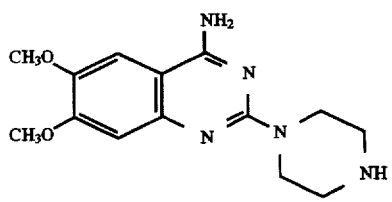

with a amine of formula VI

wherein R, $R_1$, $R_2$, n and m are as above defined in claim 1, in the presence of N,N'-carbonyldiimidazole, in an aprotic solvent, at a temperature comprised between 0° and +50° C.

22. A process for the preparation of a compound of formula (I) as defined in claim 1, wherein R is $-NR_4R_5$ group wherein $R_4$ and $R_5$ are H, which comprises hydrolysing the corresponding compounds wherein $R_4$ or $R_5$ are the group $-COOCH_2C_6H_5$, in a protic solvent, in the presence of a strong acid, at temperatures comprised between 0° C. and 40° C.

23. The process as claimed in claim 22, wherein the solvent is acetic acid, and the strong acid is hydrobromic acid.

24. A process for the preparation of a compound formula (I) as claimed in claim 1, wherein R is a group $-NR_4R_5$ wherein $R_4$ and $R_5$ are H and a methanesulfonyl group, comprising acylating with methanesulphonyl chloride the corresponding compounds wherein $R_4=R_5=H$, in aprotic solvents in the presence of a base, at a temperature comprised between 0° and 40° C.

25. The process as claimed in claim 24, wherein the aprotic solvent is pyridine and the base is triethylamine.

26. A compound as claimed in claim 1, wherein B is (B1) and A is —CO—.

27. A compound as claimed in claim 1, wherein B is (B1), A is —CO— and R is substituted aryloxy.

28. A compound as claimed in claim 1, corresponding to 4-amino-6,7-dimethoxy-2-{4-[2-(2-methoxy-6-isopropylphenoxy)acetyl]-1-piperazinyl}-quinazoline.

29. A therapeutic method for the treatment of disorders related to hyperactivity of alpha-adrenergic system, which comprises administering to a subject in need of such treatment an effective amount of at least a compound of formula (I) as defined in claim 1.

30. The therapeutic method as claimed in claim 29, wherein said disorders are selected from the group consisting of arterial hypertension, prostate benign hyperplasia, high introacular pressure and hypercholesterolemia.

* * * * *

UNITED STATES PATENT AND TRADEMARK OFFICE
CERTIFICATE OF CORRECTION

PATENT NO. : 5,798,362
DATED : August 25, 1998
INVENTOR(S) : Leonardi et al

It is certified that error appears in the above-identified patent and that said Letters Patent is hereby corrected as shown below:

On the title page, item [57] Abstract:

Line 1, "qunazolinyl-amino" should read -- quinazolinyl-amino --.

Line 7, "hpercholesterolemia" should read -- hypercholesterolemia --.

Signed and Sealed this

Sixteenth Day of March, 1999

Attest:

Q. TODD DICKINSON

Attesting Officer

Acting Commissioner of Patents and Trademarks